US010959685B2

(12) United States Patent
Flohr et al.

(10) Patent No.: US 10,959,685 B2
(45) Date of Patent: Mar. 30, 2021

(54) ASCERTAINING A FUNCTION PARAMETER RELATING TO A LOCAL TISSUE FUNCTION FOR PLURALITY OF TISSUE REGIONS

(71) Applicant: Siemens Healthcare GmbH, Erlangen (DE)

(72) Inventors: Thomas Flohr, Uehlfeld (DE); Bernhard Krauss, Burgthann (DE); Bernhard Schmidt, Fuerth (DE); Martin Sedlmair, Zirndorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/051,606

(22) Filed: Aug. 1, 2018

(65) Prior Publication Data

US 2019/0038239 A1 Feb. 7, 2019

(30) Foreign Application Priority Data

Aug. 3, 2017 (EP) ..................... 17184699

(51) Int. Cl.
*G06K 9/00* (2006.01)
*A61B 6/03* (2006.01)
(Continued)

(52) U.S. Cl.
CPC .............. *A61B 6/032* (2013.01); *A61B 5/055* (2013.01); *A61B 5/4504* (2013.01); *A61B 6/505* (2013.01);
(Continued)

(58) Field of Classification Search
CPC ....... A61B 6/032; A61B 8/087; A61B 8/5223; G06T 7/12; G06T 7/0014
(Continued)

(56) References Cited

U.S. PATENT DOCUMENTS 6,424,732 B1 * 7/2002 Shiffman ................. G06K 9/38
382/128
6,785,409 B1 * 8/2004 Suri ...................... G06T 7/0012
382/106
(Continued)

FOREIGN PATENT DOCUMENTS

CN 1502310 A 6/2004
CN 101779956 A 7/2010
(Continued)

OTHER PUBLICATIONS

Extended European search report 17184699.1 dated Feb. 26, 2018.
(Continued)

*Primary Examiner* — Marceau Milord
(74) *Attorney, Agent, or Firm* — Harness, Dickey & Pierce, P.L.C.

(57) ABSTRACT

A method for determining a local tissue function of tissue in a body region of interest of an examination object is disclosed. In an embodiment, the method includes segmentation of an outer contour of the tissue using at least one medical image recording representing the body region of interest of the examination object comprising the tissue; subdivision of the segmented tissue into at least two tissue regions; and ascertaining a function parameter relating to the tissue function for each of the at least two tissue regions. Embodiments also relate to a corresponding computing unit for determining a tissue function of tissue, a corresponding medical imaging system, a computer program and a computer-readable data carrier.

21 Claims, 4 Drawing Sheets

(51) Int. Cl.
*A61B 5/055* (2006.01)
*A61B 5/00* (2006.01)
*A61B 6/00* (2006.01)
*G06T 7/00* (2017.01)
*A61B 8/08* (2006.01)
*G06T 7/12* (2017.01)

(52) U.S. Cl.
CPC .......... *A61B 6/5217* (2013.01); *A61B 8/0875* (2013.01); *A61B 8/5223* (2013.01); *G06T 7/0014* (2013.01); *G06T 7/12* (2017.01); *A61B 6/481* (2013.01); *A61B 8/085* (2013.01); *G06T 2207/10088* (2013.01); *G06T 2207/30008* (2013.01)

(58) Field of Classification Search
USPC .................................................. 382/128, 132
See application file for complete search history.

(56) References Cited

U.S. PATENT DOCUMENTS

| | | | | |
|---|---|---|---|---|
| 7,209,587 | B1* | 4/2007 | Hsu | G06K 9/0063 |
| | | | | 382/173 |
| 7,639,855 | B2* | 12/2009 | Matsumoto | G06T 7/60 |
| | | | | 382/131 |
| 7,657,073 | B2* | 2/2010 | Sun | G06T 7/35 |
| | | | | 382/128 |
| 8,478,029 | B2* | 7/2013 | Tolliver | G06T 7/90 |
| | | | | 382/162 |
| 8,824,752 | B1* | 9/2014 | Fonte | G06T 7/0012 |
| | | | | 382/126 |
| 9,629,615 | B1* | 4/2017 | Tavakoli | G06T 7/269 |
| 10,373,718 | B2* | 8/2019 | Menon | A61B 6/501 |
| 10,413,253 | B2* | 9/2019 | Oh | G16H 10/60 |
| 2004/0101176 | A1 | 5/2004 | Mendonca et al. | |
| 2004/0101179 | A1* | 5/2004 | Suryanarayanan | G06T 7/0012 |
| | | | | 382/128 |
| 2004/0242994 | A1 | 12/2004 | Brady et al. | |
| 2009/0296999 | A1 | 12/2009 | Raundahl et al. | |
| 2011/0285702 | A1 | 11/2011 | Hautvast | |
| 2012/0052010 | A1 | 3/2012 | Sorensen et al. | |
| 2012/0280135 | A1 | 11/2012 | Bal | |
| 2013/0004044 | A1* | 1/2013 | Ross | G06T 7/136 |
| | | | | 382/131 |
| 2014/0241606 | A1 | 8/2014 | Park et al. | |
| 2014/0303487 | A1* | 10/2014 | James | A61B 5/0042 |
| | | | | 600/415 |
| 2014/0343586 | A1* | 11/2014 | Sakuragi | A61B 5/7485 |
| | | | | 606/167 |
| 2015/0071519 | A1 | 3/2015 | Foertsch et al. | |
| 2016/0148375 | A1* | 5/2016 | Oh | G06T 11/008 |
| | | | | 382/131 |
| 2016/0180042 | A1* | 6/2016 | Menon | A61B 6/501 |
| | | | | 705/2 |
| 2016/0235330 | A1 | 8/2016 | Breeuwer et al. | |
| 2016/0310018 | A1* | 10/2016 | Fonte | A61B 6/5217 |
| 2017/0128032 | A1* | 5/2017 | Buchert | A61B 5/0042 |
| 2017/0165501 | A1* | 6/2017 | Rapaka | A61N 5/1031 |
| 2018/0182102 | A1* | 6/2018 | Jerebko | G06T 7/0014 |
| 2018/0192866 | A1* | 7/2018 | Abou Shousha | A61B 3/1005 |
| 2018/0360402 | A1 | 12/2018 | Carmi | |
| 2019/0311805 | A1* | 10/2019 | Linguraru | G06K 9/6256 |
| 2020/0229679 | A1* | 7/2020 | Zhao | A61B 1/00165 |

FOREIGN PATENT DOCUMENTS

| | | |
|---|---|---|
| CN | 102301393 A | 12/2011 |
| CN | 102458482 A | 5/2012 |
| CN | 102656607 A | 9/2012 |
| CN | 105848577 A | 8/2016 |
| DE | 102013220018 A1 | 4/2014 |
| DE | 102013218047 B3 | 1/2015 |
| DE | 102015221877 A1 | 5/2017 |
| EP | 1407283 | 4/2004 |
| EP | 2810598 A1 | 12/2014 |
| WO | WO-2007090892 A1 | 8/2007 |
| WO | WO-2017103037 A1 | 6/2017 |

OTHER PUBLICATIONS

Office Action for Chinese Patent Application No. 201810859391.0 dated Mar. 23, 2020.
Office Action for Chinese Patent Application No. 201810859391.0 dated Sep. 3, 2020.

* cited by examiner

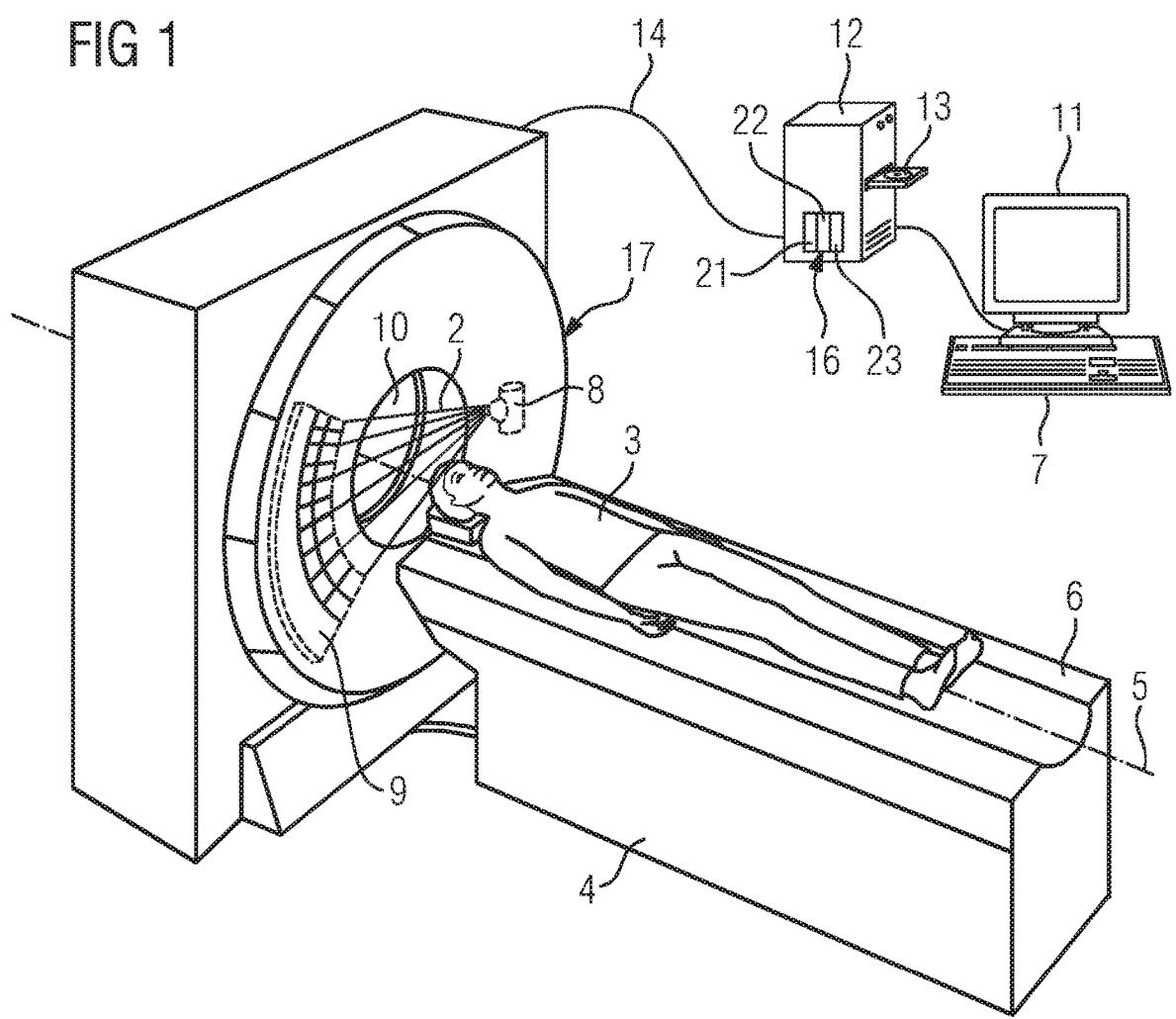

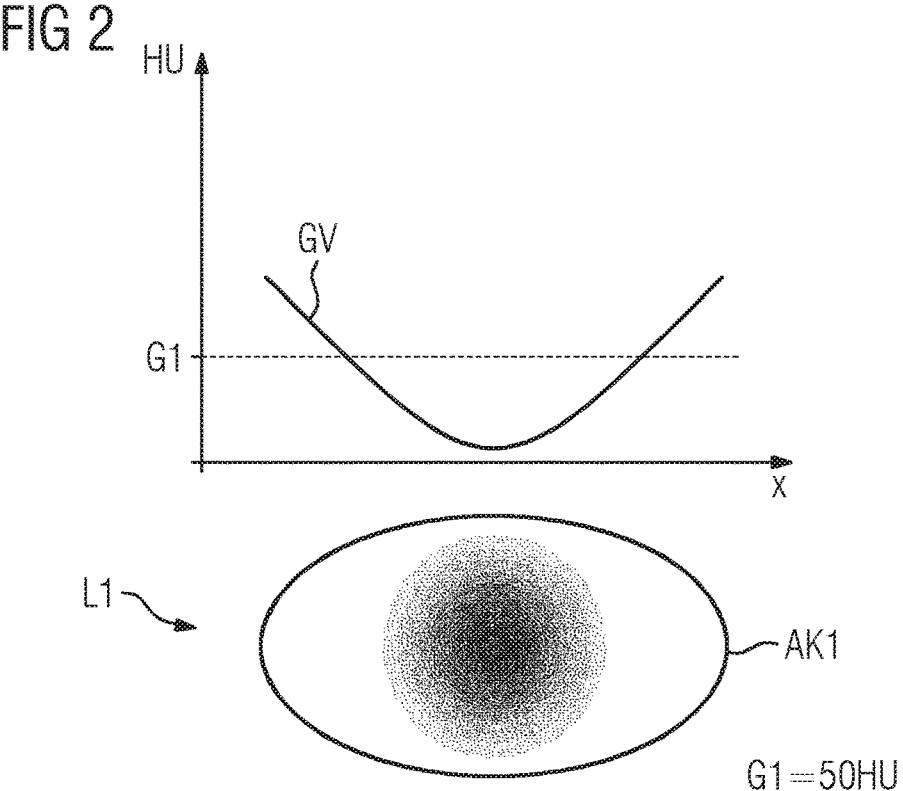
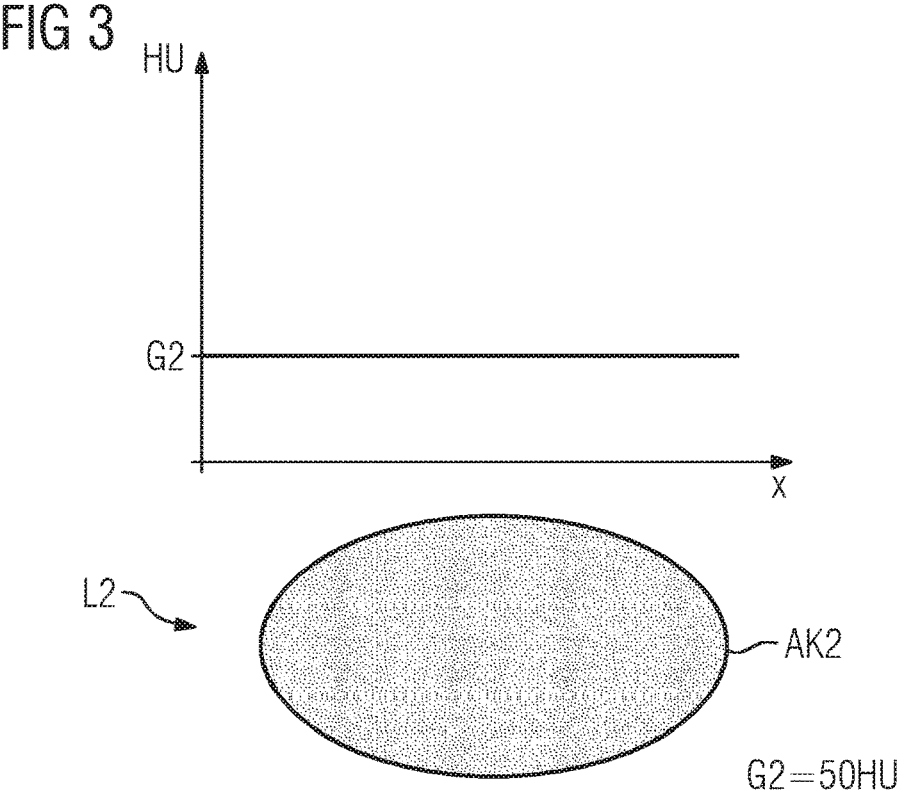

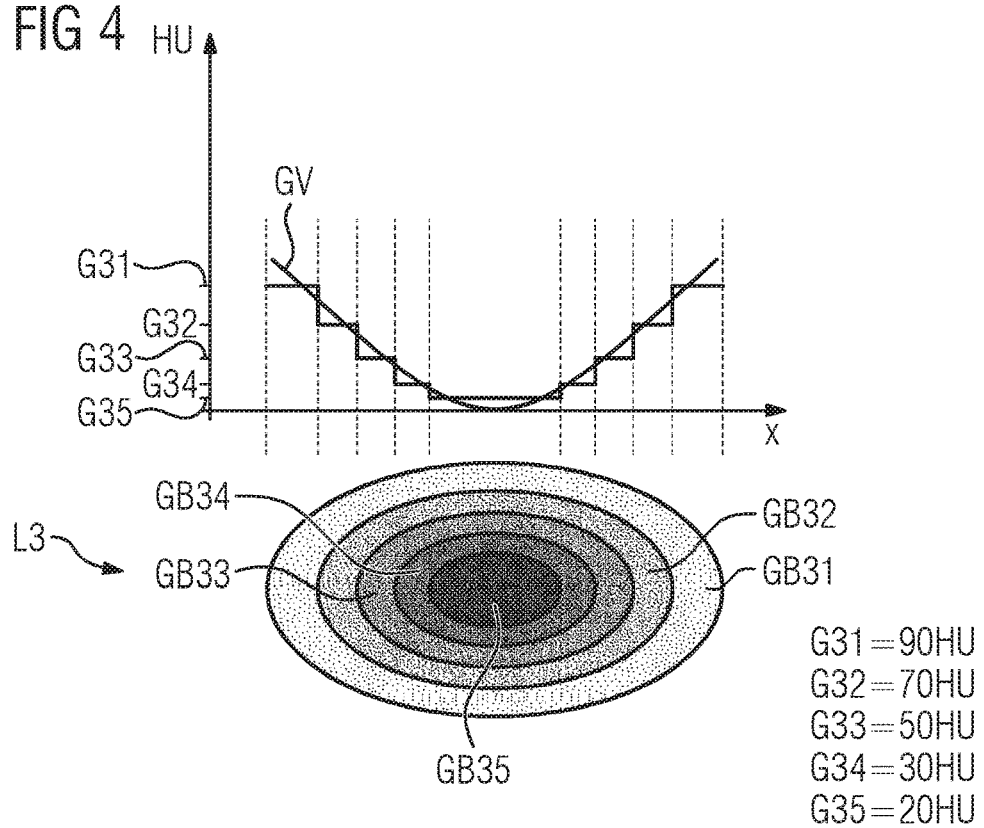
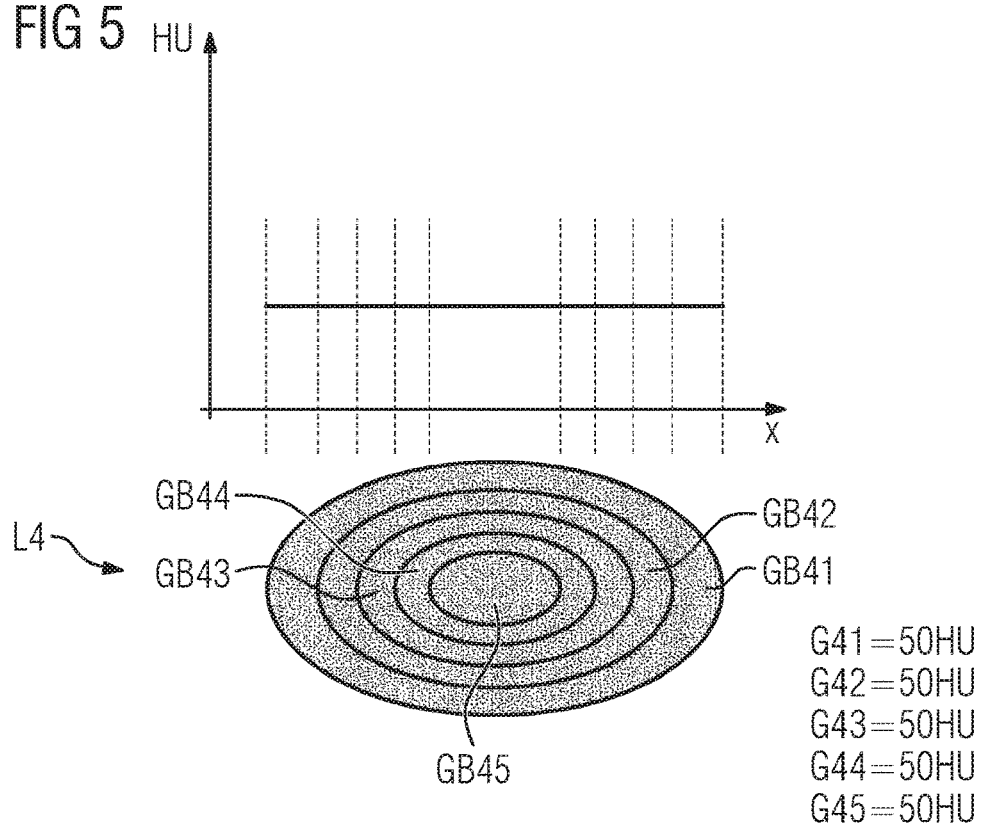

ASCERTAINING A FUNCTION PARAMETER RELATING TO A LOCAL TISSUE FUNCTION FOR PLURALITY OF TISSUE REGIONS

PRIORITY STATEMENT

The present application hereby claims priority under 35 U.S.C. § 119 to European patent application number EP17184699.1 filed Aug. 3, 2017, the entire contents of which are hereby incorporated herein by reference.

FIELD

At least one embodiment of the application generally relates to ascertaining a function parameter relating to a local tissue function for plurality of tissue regions.

BACKGROUND

Apart from surgical removal of a tumor, conventional tumor therapy includes chemotherapy, during which a patient is given cytotoxic or cytostatic drugs for targeted killing of tumor cells or the prevention of tumor growth. It also includes radiation therapy during which a tumor is treated with ionizing or particle radiation, which is also intended to kill tumor cells. Tumor response is frequently ascertained using so-called RECIST criteria. Standard RECIST criteria are, for example, the long-axis diameter (LAD) or short-axis diameter (SAD) of a tumor, i.e. substantially information on the size of the tumor measured at a specific time of observation. Disappearance or shrinkage of the tumor ascertained over a treatment period by way of by RECIST criteria, in particular without the appearance of new lesions, is an indication of complete tumor response (CR) or partial tumor response (PR). In other words, the tumor is responding to the therapy used. The treatment is successful. The ascertainment of a constant tumor size over the treatment period is an indication of a stable disease (SD), which can also correspond to a successful outcome of the treatment. An increase in the size of the tumor or the appearance of new lesions is indicative of progressive disease (PD) and ultimately of the failure of the selected treatment method.

There are also more modern tumor treatment methods, such as, for example anti-angiogenesis or immunotherapy. Anti-angiogenesis is aimed at the use of drugs to restrict the blood supply to tumor tissue by inhibiting the growth of blood vessels within the tumor. Immunotherapy helps the body's own immune system to destroy tumor cells that would otherwise evade the body's own immune response.

Conventional treatment methods cause the size of the tumor to remain the same or to be reduced. However, at least for a transitional period, novel treatment methods often have no impact on the size of the tumor or can even result in tumor growth. The desired reduction is only seen after a longer duration of treatment. In addition, more recent therapeutic forms can cause structural changes to tumor tissue, for example necrosis inside the tumor.

Not least from an economic viewpoint, time is a critical factor in cancer therapy and hence it is important to ascertain the response to the selected therapy as early as possible. Due to the different mode of action of novel therapies, conventional criteria, such as RECIST, are found to be inaccurate or even false and hence these cannot be used in the specified time frames or can only be used to a restricted extent. Therefore, novel therapeutic procedures require criteria that enable conclusions to be drawn regarding the response of tumor cells to treatment, for example their local blood supply.

It is known to use contrast medium administration with quantitative, medical imaging methods, such as, for example, computed tomography (CT) with two different energy spectra (dual energy) or dynamic perfusion CT to depict perfusion or blood volume in tumor tissue in that, for example, the accumulation of contrast medium in tumor tissue is ascertained. To date, blood volume has been evaluated for the entire lesion and hence local differences in the blood supply or local changes to the blood vessel structure have not been taken into account. In other words, the blood volume ascertained in this way corresponds to an average blood volume across the entire lesion.

Although a manual definition or selection of regions of interest (ROIs) for analysis of local blood volume can identify local differences, this is heavily user dependent and hence poorly reproducible and fundamentally error-prone.

Alternative analytical methods, such as, for example, known texture analysis methods are supposedly able to use an evaluation of the structural properties of the depicted tumor tissue to create so-called multi-dimensional 'perfusion maps' for a tumor, but these react very sensitively to the smallest changes in the processing chain (reconstruction core, slice thickness, noise filter, etc.). Neither do these methods enable a comparison of initial and control measurements.

SUMMARY

At least one embodiment of the present invention provides an alternative method/system that enable conclusions relating to local tissue function to be drawn in a reliable and reproducible manner. In particular, at least one embodiment of the present invention derives information on local perfusion at an early stage after the commencement of therapy.

Embodiments of the present application are directed to a method for determining a tissue function of tissue, a corresponding computing unit and a medical imaging system, a corresponding computer program and/or a corresponding computer-readable data carrier. Preferred and/or alternative advantageous variants are the subject matter of the claims.

The following describes embodiments of the method and devices. Features, advantages or alternative embodiments mentioned herein can also be transferred to the other subject matter and vice versa. In other words, material claims (which are, for example, directed at a method) can also be developed with features which are described or claimed in connection with one of the devices. Herein, the corresponding functional features of the method are formed by corresponding material modules or units.

An embodiment of the present invention relates to a method for determining a local tissue function of tissue in a body region of interest of an examination object.

In at least one embodiment the method includes:

segmenting an outer contour of the tissue using at least one medical image recording representing the body region of interest of the examination object including the tissue, to produce a segmented tissue;

subdividing the segmented tissue into at least two tissue regions; and ascertaining a function parameter relating to a tissue function for each of the at least two tissue regions.

An embodiment of the present invention relates to a computing unit for determining a tissue function of tissue in a region of interest of an examination object, the computing unit comprising:

a memory storing program computer-readable instructions; and one or more processors configured to execute the instructions such that the one or more processors are configured to, segment an outer contour of the tissue using at least one medical image recording representing the body region of interest of the examination object including the tissue, to produce a segmented tissue, subdivide the segmented tissue into at least two tissue regions, and ascertain a function parameter relating to a tissue function for each of the at least two tissue regions.

An embodiment of the present invention relates to a medical imaging system comprising the computing unit of at least one embodiment.

An embodiment of the present invention relates to a memory, storing a computer program with program code for carrying out the method of at least one embodiment when the computer program is executed on a computer.

An embodiment of the present invention relates to a non-transitory computer-readable data carrier storing program code of a computer program for carrying out the method of at least one embodiment when the computer program is executed on a computer.

BRIEF DESCRIPTION OF THE DRAWINGS

The above-described properties, features and advantages of embodiments of the invention and also the manner in which these are achieved will become clearer and more plainly comprehensible in conjunction with the following description of the example embodiments explained in more detail in conjunction with the drawings. This description does not restrict the invention to these example embodiments. In different figures, the same components are given identical reference characters. The figures are generally not shown true to scale. In the drawings:

FIG. 1 shows a view of a medical imaging system in the form of a computed tomography scanner according to one embodiment of the present invention, FIG. 2 shows a lesion in a known medical image recording, FIG. 3 shows another lesion in a known medical image recording, FIG. 4 shows a lesion in a medical image recording according to an example embodiment of the present invention, FIG. 5 shows another lesion in a medical image recording according to an example embodiment of the present invention.

DETAILED DESCRIPTION OF THE EXAMPLE EMBODIMENTS

Figure 6:
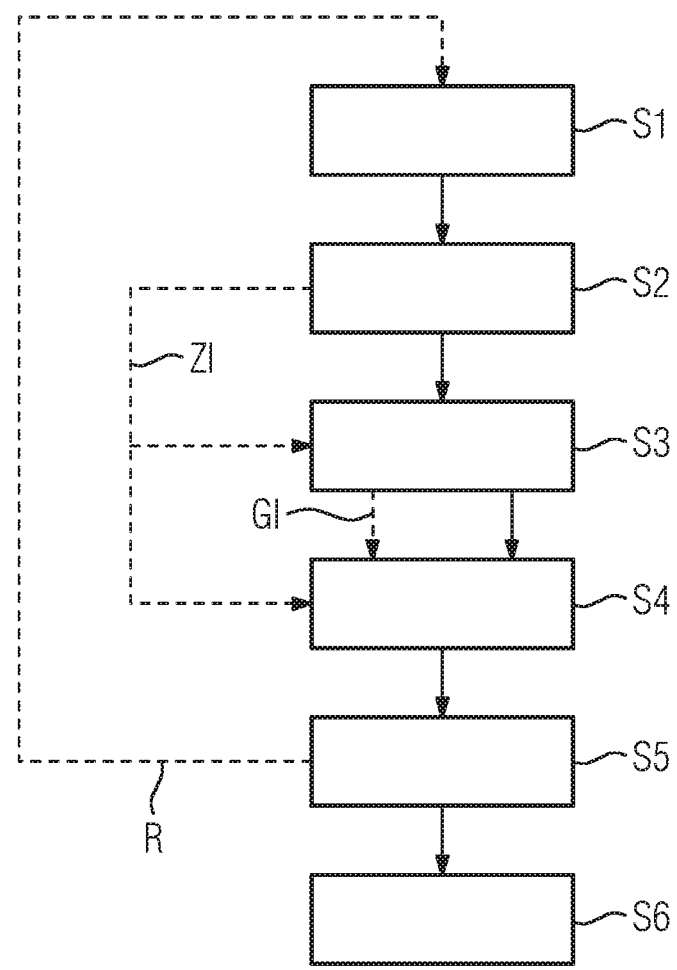
FIG. 6 shows a schematic representation of a method according to an example embodiment of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally)

between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention is directed at ascertaining a tissue function of tissue in a body region of interest of an examination object. Herein, the method pays particular attention to ascertaining this tissue function on an individual basis for local regions of tissue. In other words, the method enables the depiction of local differences in the tissue function.

For the purposes of at least one embodiment of the invention, a tissue function designates a physical, chemical, functional and/or structural property of tissue, such as, for example, a material density, a material or substance content or component, a substance accumulation rate (in the case of dynamic measurements) or the like.

For the purposes of embodiments of the invention, tissue should be understood as being a plurality of similarly embodied, generally cohesive body cells that exert the same or similar function. In other words, tissue corresponds to a tissue type or a tissue sort. Tissue can, for example, be an organ, a partial organ or a partial region of an organ, such as pulmonary, epithelial or renal tissue. For the purposes of the invention, tissue can also comprise or form a lesion, i.e. an anomalous change. For the purposes of the invention, tissue may comprise only one or more tissue types.

The tissue is located in a body region of interest. For the purposes of the present invention, this corresponds to the part of the body to be examined or region of the body to be examined, for example the abdomen or the skull. In this context, the body region to be examined corresponds to the part of an examination object, which is to be examined or depicted via a medical imaging system, for example a computed tomography scanner.

Insofar, in the following, it is assumed without restricting the generality that the examination object is a patient, generally a human being. In principle, the patient can also be an animal. Therefore, in the following, the two terms "examination object" and "patient" are used synonymously. The examination object can alternatively be a plant or a non-living object, for example a historical artifact or the like.

The segmentation of an outer contour of the tissue using at least one medical image recording representing the body region of interest of the examination object comprising the tissue corresponds to a first method step.

A medical image recording is a multi-dimensional, in particular two-dimensional or three-dimensional, depiction of sensor data belonging to the body region of interest, which was generated via a medical imaging system. The medical image recording can be a computed tomography recording, MRI recording, X-ray recording, positron emission tomography (PET) recording, X-ray C-arm recording, ultrasound recording, single-photon emission computed tomography (SPECT) recording or the like. The medical image recording can be a single recording or also a partial object in a multislice series of recordings.

The dimensions of the image recording indicate whether a selected slice with a defined slice thickness (2D) of the region of interest or a selected volume (3D) is depicted. In the case of a plurality of medical image recordings, the depiction of the tissue can be three- or four-dimensional, i.e. with or without time history (3D or 4D). Medical image recordings with time history are generally functional or dynamic image recordings, for example a perfusion measurement. A plurality of medical image recordings can also comprise individual recordings of different energy spectra. A medical image recording can also be a constructed or composite image compiled from a plurality of individual recordings, in particular with different recording techniques, or comprising image information from a plurality of individual recordings. In other words, a medical image recording can be depicted as at least one recording from the following group of recordings: a two-dimensional tomographic image, a three-dimensional image, a four-dimensional image or a multi-spectral image.

The image acquisition can be time-correlated with the performance of the method according to of at least one embodiment of the invention. Alternatively, the medical image recording can be acquired any time prior to the method of at least one embodiment of being carried out.

In a first step of at least one embodiment, the outer contour of the tissue under consideration is segmented in the medical image recording. In other words, the tissue to be examined is delimited outwardly and its outer contour defined. The outer contour can be an open or enclosed line (2D) or area (3D) depending on the size of the field of view (FoV) selected during the image acquisition. This separates the tissue from the surrounding structures. The segmentation can be performed automatically, semi-automatically using segmentation algorithms known in the art or manually in the image recording by a user.

A second step of the method according to at least one embodiment of the invention is the subdivision of the segmented tissue into at least two tissue regions. In other words, for the tissue, at least two subregions are formed and arranged with the segmented outer contour of the tissue thus representing a substructure of the tissue. The number and the arrangement of the tissue regions with respect to one another are variable and can in particular depend on the size or type of the tissue examined. Alternatively or additionally, the number and location of the tissue regions can be determined in dependence on the choice of the function parameter to be ascertained subsequently. The subdivision is preferably performed automatically, but can also be performed semi-automatically, for example, in that the user is first shown a suggestion or a selection of suggestions for confirmation or selection. The subdivision is further preferably performed based on empirical or reference values. In other words, standard subdivisions of the segmented tissue for specific tissue types, tissue sizes, function parameters under consideration and/or the like can, for example, be held in a database and included as a reference or as reference values in the subdivision or taken into account thereby. Preferably, the definition of the location and/or size of the tissue regions also includes, where known, information, empirical values or assumptions regarding a spatial distribution of the function parameter to be ascertained subsequently. Thus, the method according to the invention advantageously ensures that local fluctuations in the tissue function are depicted.

In a third step of at least one embodiment, as already indicated above, a function parameter relating to the tissue function is ascertained for each of the at least two tissue regions. The function parameter is a measure, representative or characteristic value for the tissue function. In other words, a function parameter characterizes a specific tissue function or enables conclusions to be drawn regarding this tissue function. According to the invention, the ascertaining comprises a quantitative and/or qualitative evaluation of image information contained in the medical image recordings, in each case with respect to the individual tissue regions. For example, in the case of CT-image recording with contrast medium administration, an evaluation of the brightness values of the image elements (HU values) can be performed for each tissue region thus enabling conclusions to be drawn regarding the (average) perfusion of tissue in each of the tissue regions.

Alternatively, it is also possible to ascertain more than only one function parameter per tissue region. Insofar, the method according to at least one embodiment of the invention can be used to investigate a plurality of tissue functions in parallel.

To summarize, therefore, the inventors have recognized that the method according to at least one embodiment of the invention enables the depiction of spatial fluctuations or differences in a tissue function in that a function parameter characteristic of a tissue function is determined individually for different tissue regions, i.e. for at least two tissue regions. Therefore, the local values of the function parameter determined in this way for the different tissue regions serve as a measure for the homogeneity or inhomogeneity of a tissue function across the tissue under examination. Hence, the method according to the invention is suitable for a plurality of different medical applications.

The method according to at least one embodiment of the invention is in particular suitable for use when examining the response behavior of tumor diseases, for monitoring the profile of any other diseases, such as, for example, osteoporosis, or, more generally, also for performing checkups at a later time, because the subdivision of the segmented tissue and the ascertainment of the function parameter according to embodiments of the inventions, as performed in an initial first examination, can be transferred to image recordings for a later checkup measurement in a robust and reproducible manner and hence produces data comparable to the first examination.

Finally, it is mentioned once again that the described method steps, i.e. segmentation, subdivision and ascertainment in the medical image recordings can be pixel-based and/or voxel-based.

According to one embodiment of the present invention, the at least two tissue regions are arranged in slices such that a first tissue region completely encloses a second tissue region. In other words, the tissue regions are arranged in a ring-shape or interleaved so that only one outer tissue region lies externally on the segmented outer contour of the tissue or encloses this and comprises the other tissue regions internally. This arrangement corresponds to an onion-layer-like construction. It is particularly suitable for the examination of tissue functions of tumor tissue or lesions of an unknown nature suspected of being tumor tissue since these frequently comprise both structural and functional differences between the core and edge regions. The suggested arrangement of the tissue regions enables these differences to be particularly advantageously taken into account or resolved.

Alternative arrangements, such as, for example, a quadrant-like or layer-like subdivision of the tissue regions, are also conceivable and in compliance with the invention as long as they have been found to be suitable for the specific application.

According to a further embodiment of the present invention, the outer contour of the at least two tissue regions each has the same shape as the outer contour of the segmented tissue. This means that the profile of the outer contour of each tissue region is morphologically identical to the profile of the outer contour of the segmented tissue. Only the size of the outer contours differs. This corresponds to a particularly preferred variant of the invention because this makes subdivision into the tissue regions particularly simple since the shape or profile of the outer contours was already defined with the segmentation of the tissue. This procedure is in particular used when the outer contour can be uniquely defined in the medical image recording by way of segmentation.

Insofar, in a particularly preferred embodiment of the invention, the subdivision of the segmented tissue is performed by way of a morphological operation. Morphological operations are known as imaging processing mechanisms in the art. Herein, this entails operations that are generally applied to the structure of an object with the aim of effecting a change to the structure, eliminating disruptions such as occur following segmentation, calculating specific shape features or detecting specific shapes in an image. In the present case, the object corresponds to the tissue examined, the outer contour of which has already been segmented. Herein, the segmented outer contour corresponds to the structure of the object. The object should advantageously be present in the form of a binary image for processing via a morphological operator. In the present case, it is, for example, possible to use an erosion operator for the determination of the profiles of outer contours of a plurality of tissue regions in order to achieve a desired reduction of the segmented outer contour. The contour profiles determined in this way for the individual tissue regions can then be transferred or integrated into the medical image recording, for example by way of image addition or superimposition.

This configuration or division and arrangement of the tissue regions corresponding to the shape or profile of the segmented outer contour of the tissue represents the best possible way of taking account of the geometry of the tissue.

According to another preferred embodiment, the outer contours of the at least two tissue regions have a distance from one another within the range of 0.2 mm to 2.0 mm. In other words, the outer contours of adjacently arranged tissue regions are spaced apart as disclosed above. As already mentioned above, the specific location and size of the tissue regions depends on different factors of the individual examination object, such as, for example, the size of the tissue, structure of the tissue, reason for the examination, function parameters to be evaluated or the like. However, it has been found in practice that tissue regions with a radial extension in a range between 0.2 mm and 2.0 mm produce particularly good results with respect to spatial inhomogeneity of a tissue function.

According to a further preferred embodiment of the present invention, the segmented tissue comprises a medical lesion. In other words, the segmented tissue can comprise healthy tissue and lesion tissue. Alternatively and according to a main application of at least one embodiment of the present invention, the segmented tissue is exclusively formed by a lesion.

In a further example of at least one embodiment of the present invention, the segmented tissue does not comprise a lesion. For the purposes of at least one embodiment of the invention, a lesion should be understood to be a spatially extended structure that is conspicuous in a medical context, such as, for example, untypical or unexpected depiction properties in medical imaging and/or an atypical function, for example a changed metabolic activity. A lesion can in particular be a tumor, however, this also includes other, in particular malignant, lesions.

According to another embodiment of the present invention, the function parameter is at least a parameter from the following group of parameters: blood flow, iodine-accumulation, iron-accumulation, calcium density, fat content.

The first three function parameters can be ascertained particularly effectively when a CT perfusion recording is used as a medical image recording. With CT perfusion, the perfusion of tissue, for example the brain, liver or heart is measured with the aid of contrast media, in particular iodine-containing or iron-containing contrast media, and special post-processing software. With CT perfusion, after intravenous contrast-medium injection, the body region of interest is repeatedly scanned over a specific period, for example 40 s to produce a 4-dimensional image dataset that provides information on influx and efflux of the contrast medium.

In addition to blood flow, which indicates how much blood (ml) flows through a mass of tissue (g) within a given time (min), it is also possible to evaluate further parameters, such as, for example, the blood volume, i.e., the volume flow (ml) identified per mass of tissue (g), or tissue permeability, i.e. the amount of volume flow (ml) per mass of tissue (g)

that arrives within a given time (min) in the tissue of interest, and, for example, depict them in color form in a color map.

Function parameters, such as calcium density or fat content can preferably be derived based on spectrally resolved medical image recordings by way of the material decomposition method known in the art. Herein, spectrally resolved image recordings can in particular be generated via multi-spectral computed tomography, for example with dual source tomography.

On the basis of the evaluation of one of the named function parameters, the method according to the invention in particular provides information regarding the spatial distribution and inhomogeneity of a blood supply to the tissue examined, which in particular enables conclusions to be drawn regarding a response or reaction of the tissue to a therapeutic measure performed.

According to a further embodiment of the invention, the function parameter is at least one typical parameter for texture analysis from the following group of parameters: average density, moment, heterogeneity, entropy, fractal dimension.

For the purposes of at least one embodiment of the invention, texture analysis generally refers to the characterization of specific regions or areas of a medical image recording by their texture content; in other words, texture analysis evaluates a function of a spatial distribution or change to pixel or voxel-intensity values. For example, texture analysis corresponds to a quantitative measurement of variables, such as entropy, curvature or obliquity, which, with respect to a surface depicted in the image recording, can be derived from the above-named intensity values. As partially mentioned above, textures in medical image recordings can, for example, be different (average) tissue densities, different tissues or tissue types, different surface properties or the like. Texture analysis is typically performed in at least one color channel, for example of a gray-scale image or a red, green and/or blue color channel, of a medical image recording. Herein, a color channel can in particular characterize a special recording technique, for example different spectra of detected radiation.

Insofar, the function parameter ascertained according to this embodiment can be a texture metric in the sense of a pixel-intensity metric, a pixel-variance metric, a pixel-correlation metric, a metric relating to a spatial change and/or a metric relating to a frequency change.

According to a particularly preferred embodiment of the present invention, ascertaining a function parameter comprises a texture analysis, which in turn comprises determination of a feature vector based on intensity values of image elements of the medical image recording, application of a machine learning method to the feature vector and generation of the function parameter as a result of the machine learning method.

In other words, the method according to at least one embodiment of the invention provides for application of machine learning algorithms to picture elements, i.e. pixels or voxels of the medical image recording in order to determine the function parameter. For example, before an application, an algorithm can be trained using training images, with or without the assistance of a user, to recognize special features and derive a function parameter. The machine learning method can, for example, be an artificial neural network known in the art, a deep belief method or the like.

According to a further embodiment of the invention, the medical image recording is an image recording from the following group of image recordings: single-energy recording, multi spectral computed-tomography recording, perfusion-computed-tomography recording, ultrasound recording, magnetic-resonance recording and perfusion-magnetic-resonance recording or the like. Depending upon the type of image recording, as already mentioned above, contrast medium administration can be involved in the data acquisition.

At least one embodiment of the invention further relates to a computing unit for determining a tissue function of tissue in a region of interest of an examination object comprising a processor for carrying out the method according to at least one embodiment of the invention.

At least one embodiment of the invention also relates to a medical imaging system with a computing unit according to at least one embodiment of the invention. Advantageously, the computing unit is integrated in the medical imaging system. Alternatively, the computing unit can include at least one processor and can also be arranged in a remote or separate location. The computing unit can in particular be embodied to carry out the step of ascertaining a function parameter relating to the tissue function for each of at least two tissue regions, but also the entire method according to the invention, for a medical imaging system or for a plurality of systems, for example in a radiology center or hospital with a plurality of magnetic-resonance systems.

At least one embodiment of the invention further relates to a computer program with program code for carrying out the method according to at least one embodiment of the invention for determining a tissue function of tissue in a region of interest of an examination object when the computer program is executed on a computer.

At least one embodiment of the invention further relates to a computer-readable data carrier with program code of a computer program for carrying out the method according to at least one embodiment of the invention for determining a tissue function of tissue in a region of interest of an examination object when the computer program is executed on a computer. Advantageously, in particular the ascertaining of a function parameter relating to the tissue function for each of at least two tissue regions can be executed on a computer, for example in a computing unit of a medical imaging system.

FIG. 1 shows a medical imaging system in the form of a computed tomography scanner. The computed tomography scanner shown here has a recording unit 17, comprising an X-ray source 8 and an X-ray detector 9. During the recording of X-ray projections, the recording unit 17 rotates about a system axis 5, and the X-ray source 8 emits X-rays 2 during the recording 2.

During the recording of X-ray projections, a patient 3 lies on a patient bench 6. The patient bench 6 is connected to a base of the bench 4 such that the base bears the patient bench 6 with the patient 3. The patient bench 6 is designed to move the patient 3 along a recording direction through the opening 10 in the recording unit 17. The recording direction is generally defined by the system axis 5 about which the recording unit 17 rotates during the recording of X-ray projections. In this example, is the body axis of the patient 3 is the same as the system axis 5. In the case of a spiral recording, the patient bench 6 is moved continuously through the opening 10 while recording unit 17 rotates about the patient 3 and records X-ray projections. As a result, the X-rays 2 describe a spiral on the surface of the patient 3.

In an embodiment, the computed tomography scanner includes a data-processing facility 12 in the form of a computer, which is connected to a display unit 11, for example for the graphical display of medical image recordings, here in the form of computed tomography recordings, and an input unit 7. The display unit 11 can, for example, be an LCD, plasma or OLED screen. It can furthermore be a touch-sensitive screen, which is also embodied as an input unit 7. A touch-sensitive screen of this kind can be integrated in the imaging device or embodied as part of a mobile device. The input unit 7 is, for example, be a keyboard, a mouse, a so-called "touch screen" or even a microphone for voice input. The input unit 7 can also be configured to recognize movements of a user and translate them into corresponding commands. The input unit 7 can, for example, be used by a user to confirm the segmentation of an outer contour of tissue in a body region of interest performed automatically by the computer 12. A user can also use the input unit 7 can to confirm or adapt an automatically performed subdivision of the segmented tissue into plurality of tissue regions or to perform a manual subdivision into tissue regions.

The computer 12 is connected to the rotatable recording unit 17 for data exchange. The connection 14 is used, on the one hand, to transmit control signals for the data acquisition from the computer 12 to the recording unit 17 and, on the other, projection data recorded for the patient 3 can be transmitted to the computer 12 for image reconstruction by way of standard reconstruction methods. The connection 14 is implemented in a known way either with a cable connection or wirelessly.

According to this example embodiment, the data-processing facility 12 in form of the computers comprises a locally arranged computing unit 16. The computing unit 16 is embodied as an image- or image-data-processing unit. It includes a memory and at least one processor to carry all the computing steps relating to the method according to embodiments of the invention on a medical image recording recorded by the recording unit 17. However, the medical image recording can however also be provided by another medical imaging system of the computing unit 16 and does not have the acquired in a time immediately before further processing of the image dataset by the computing unit 16. For example, the image dataset can be supplied to the computing unit 16 via a mobile computer-readable data carrier, which is known per se, via a hospital or radiology information system (HIS or RIS) or via the internet in a way which is known per se.

To carry out the method according to at least one embodiment of the invention, the computing unit 16 including the at least one processor comprises a segmentation unit 21 for the segmentation of the outer contour of the tissue to be examined in the medical image recording. The segmentation is performed automatically or semi-automatically, but it can also, for example, be performed entirely manually by a user in dependence on the quality of the medical image recording or in dependence on the function parameter to be ascertained. In addition, the computing unit 16 also comprises a dividing unit 23, which is configured to divide, the segmented tissue into at least two tissue regions. To this end, the dividing unit can be in data connection with the computer 12 in order to receive information on the scan protocol for the data acquisition or the underlying medical question at issue in order automatically to define the number, size and/or location etc. for the tissue regions.

In addition, the computing unit 16 also comprises an ascertaining unit 22, which is configured to ascertain a function parameter relating to the local tissue function for each of the tissue regions. To this end, the ascertaining unit 22 evaluates image information based at picture-element level, i.e. pixel-based or voxel-based, in particular intensity values, transfers these for each of the tissue regions into a value for the function parameter under consideration. Depending upon the function parameter to be ascertained, a different analysis specification or analysis for evaluation can be held in a memory, in particular a memory of the data-processing system 12 (not shown), to which the ascertaining unit 22 has access in order to select the correct specification for the image analysis.

The computing unit 16 can interact with a computer-readable data carrier 13, in particular to carry out a method according to at least one embodiment of the invention by way a computer program with program code. Furthermore, the computer program can be stored for retrieval on the machine-readable carrier. In particular, the machine-readable carrier can be a CD, DVD, Blu-ray disc, a memory stick or a hard disk. The computing unit 16, and hence, also its subcomponents can be embodied in the form of hardware or in the form of software. For example, the computing unit 16 is embodied as a so-called FPGA (abbreviation for "Field Programmable Gate Array") or comprises an arithmetic logical unit. Alternatively, individual subcomponents or all subcomponents can be arranged in decentralized locations, for example individual computing steps of the method can be carried out in a central computer center of a medical service providing facility, for example hospital, or in the Cloud. Herein, in particular data protection and patient protection should be taken into account during the data exchange.

In the embodiment shown here, at least one computer program is stored in a memory of the data-processing system 12, which carries out all method steps of the method according to at least one embodiment of the invention when the computer program is executed on the computer 12. The computer program for carrying out the method steps of the method according to at least one embodiment of the invention comprises program code. Furthermore, the computer program can be embodied as an executable file and/or stored on a different computing system other than the computer 12. For example, the computed tomography scanner can be designed such that the computer 12 loads the computer program for carrying out the method according to at least one embodiment of the invention into its internal memory via an intranet or via the internet.

FIG. 2 shows by way of example a lesion L1 in a medical image recording according to the prior art. The lesion can, for example, be tumor-like tissue. The medical image recording representing the lesion L1 corresponds to a computed tomography slice recording, which was acquired with the administration of iodine-containing contrast medium.

FIG. 3 shows by way of example a lesion L2 with the same shape and size as the lesion L1 and which, for purposes of simplicity and for illustrative purposes, was depicted using the same recording technique and procedure. Both lesions L1 and L2 were segmented by way of known segmentation algorithms; the outer contour AK1, AK2 is known in each case. For purposes of simplicity, surrounding tissue is not depicted. Known diagnostic mechanisms can be used to ascertain an average gray scale value G1, G2 (in Houndsfield Units HU) representing X-ray absorption for each lesion taking account of all the image element values, or here pixel entries, comprises by the outer contour AK1, AK2. This corresponds to an average iodine contrast or an average iodine content for each of the lesions.

It may be identified that the lesion L1 has a darker region in the center that becomes continuously lighter toward the outside. This spatial gray scale distribution GV is illustrated by way of example in FIG. 2 in the diagram arranged over the lesion L1. In other words, compared to the outer edge regions, at the time of the image data measurement, only a small amount of contrast medium has accumulated in the interior of lesion L1 thus indicating reduced perfusion of the interior of the lesion.

In contrast to this, lesion L2 has a substantially homogeneous gray scale distribution, which indicate uniform contrast medium distribution. The ascertained average gray scale values G1, G2 can be the same, or virtually the same, for both lesions L1 and L2. In-depth differentiation of a perfusion state or contrast medium distribution of the two lesions L1 and L2 is not possible, or is only qualitatively possible, using the known procedure. A conclusive decision as to whether, for example, lesion L1 is responding to a selecting form of therapy is not possible with the described known procedure since local differences in the gray scale within the lesion are 'averaged out'.

FIGS. 4 and 5 show by way of example lesions L3 and L4, each in a medical image recording according to example embodiments of the invention. The medical image recordings representing the lesions L3, L4 once again correspond to computed tomography slice recordings acquired with the administration of iodine-containing contrast medium.

Once again, lesion L4 has the same shape and size as lesion L3. Like lesion L1, there is a dark region in the center of lesion L3, which, as in the situation with lesion L1, is an indicator of reduced contrast medium uptake. This gray scale distribution GV is shown by way of example in the diagram over lesion L3 in FIG. 3. Like lesion L2, lesion L4 has a uniform gray scale distribution. The outer contours AK3, AK4 are also known by way of segmentation. For purposes of simplification, surrounding tissue is not shown.

According to at least one embodiment of the invention, the lesions L3, L4 are divided into in five tissue regions GB31, GB32, GB33, GB34, GB35 and GB41, GB42, GB43, GB44, GB45. The subdivision, i.e. the definition of size, location, arrangement and/or number of tissue regions is preferably performed automatically and/or taking into account the size, position or, if known, type or suspected type, of the lesion. In addition, based on the medical question at issue, it is also possible for a function parameter FP to be ascertained subsequently or the imaging technique used to influence the subdivision.

In the present case, an onion-layer-like division was performed in each case with a further outward tissue region, for example GB31, completely including an internal tissue region, for example GB32. Herein, the outer contours of the individual tissue regions have been selected as morphologically identical to the outer contour AK3, AK4 of the lesions L3, L4.

Subsequently, a function parameter FP is derived for each of the individual tissue regions GB31, GB32, GB33, GB34, GB35 and GB41, GB42, GB43, GB44, GB45 from the medical image recording. In this example, an average gray scale value or iodine contrast G31, G32, G33, G34, G35 or G41, G42, G43, G44, G45 is ascertained for each lesion L3, L4 for each of its tissue regions GB31, GB32, GB33, GB34, GB35 and GB41, GB42, GB43, GB44, GB45 from the respectively comprised pixel entries. The averaged iodine contrast values provide information on a local tissue function GF or indicate measure for the tissue function GF, in this case tissue perfusion, illustrated by the gray scale distribution GF. In other words, according to at least one embodiment of the invention, increased spatial resolution of a tissue function GF is achieved.

While with reference to lesion L4, a substantially constant gray scale value G41=G42=G43=G44=G45=50 HU was ascertained for all five of its tissue regions GB41, GB42, GB43, GB44, GB45, for lesion L3, the procedure according to the invention reveals clear differences in the gray scale value G31=90 HU, G32=70 HU, G33=50 HU, G34=30 HU, G35=10 HU between the individual tissue regions. By way of this spatial resolution and including an earlier medical image recording evaluated according to the invention, it is now, for example, possible to ascertain response to a therapy.

The image recording based on the evaluation according to at least one embodiment of the invention can correspond to a representation of a region of interest obtained with any kind of recording technique or can be a compilation of a plurality of individual recordings. According to at least one embodiment of the invention, it is also possible to evaluate a plurality of image recordings, in particular, if the image recordings contain functional information.

Finally, reference is made once again to the fact that, for illustrative purposes, the shape and size of the lesions and tissue regions were only selected by way of example and in particular are not true to scale. Any other shapes of examined tissue are possible.

FIG. 6 shows a schematic representation of a method according to at least one embodiment of the invention according to an example embodiment of the present invention. Step S1 comprises the reception of at least one medical image recording B of a region of interest of an examination object 3, for example a computed-tomography recording or an MRI recording in a computing unit 16. The medical image recording B can be acquired by a recording unit 17 in temporal correlation with the image evaluation according to at least one embodiment of the invention or, if has already been acquired previously, from a local or remote memory, for example a hospital PACS system, loaded into the computing unit 16. Alternatively, the medical image recording B can be generated in that image information from at least two different recordings of the region of interest are combined. Herein, it is possible to use standard imaging methods, such as, for example, material decomposition, image correction measures, such as, for example, noise suppression or the like, if necessary.

In a step S3, an outer contour of tissue contained in the medical image recording and to be examined, preferably a lesion, is segmented in the computing unit 16, in particular the segmentation unit 21. In other words, individual image elements are divided into tissue to be examined or surrounding tissue. Herein, preferably image element-based or edge-based segmentation methods are used which are known per se.

In an optional step S2, for segmentation or before segmentation by the computing unit 16, additional information ZI can be acquired on the question at issue underlying the examination or an initial suspicion or on the scan protocol used for the image acquisition in order to decide which body region of interest, and hence which tissue types, were depicted and/or which structure depicted in the medical image recording or which tissue, and/or with which quality, is to be segmented. This, for example, enables the segmentation algorithm to be selected.

Alternatively, it is possible for corresponding entry with respect to the additional information ZI to be provided by a user on request or initiatively via a user interface 7, 11 of the computing unit 16. Following segmentation, the size, i.e. the longitudinal extension in different spatial directions, the volume, the shape of the outer contour AK or the like of the tissue to be examined is known. This size information GI can also be used in subsequent steps. In a further step S4, the segmented tissue is divided into a plurality of tissue regions GB.

Preferably, more than two, in particular four to five tissue regions GB are defined. The greater the number of tissue regions GB, the greater the informative value of the subsequently ascertained function parameter FP on a local tissue function GF within the segmented tissue.

In order to find the best possible compromise between the spatial resolution of the tissue function GF required for the medical question at issue and the necessary system resources, such as computing capacity or processing, for step S4, in addition to the additional information ZI on the medical question at issue or the scan protocol (from step S2), it is also possible for size information GI on the size, volume and/or shape and/or the like of the tissue to be examined to be included in the definition of the individual tissue regions GB. To this end, a dividing unit 23 comprised by the computing unit 16 can exchange data with the segmentation unit 21 and/or the data-processing facility 12, which also controls a medical imaging system. The individual tissue regions GB are preferably interleaved within one another or, in other words, have a slice-type structure and/or each have morphologically the same outer contour as the segmented tissue. In this case, the dividing unit 23 can define the individual tissue regions by way of morphological operations, such as, for example, an erosion and/or dilation operator. In this case, the tissue regions have an outer-contour to outer-contour distance or a radial extension of 5 mm.

In a further step S5, a function parameter FP relating to tissue function GF for each of the individual tissue regions GB is ascertained. In other words, a value for the function parameter FP is derived individually, i.e. locally for each tissue region GB. This evaluation can produce different function parameter values for the individual tissue regions, which, when considered together, represent a spatial distribution of tissue function, wherein local differences in the tissue function can be resolved.

According to at least one embodiment of the invention, the ascertainment of the function parameter is taken over by the ascertaining unit 22. This is configured for the individual extraction and analysis of image information for each of the individual tissue regions, in the medical image recording. Function parameters can be: blood flow, iodine-accumulation, iron accumulation, calcium density, fat content. However, function parameter can also be typical parameters used for texture analysis, such as average density, moments, heterogeneity, entropy, fractal dimension. Accordingly, the ascertaining step can comprise a texture analysis. To this end, the ascertaining unit 22 can preferably determine a feature vector based on intensity values of the image elements in each individual tissue region. The ascertaining unit 22 can furthermore preferably use machine learning methods in order to generate at least one function based on image element entries and/or the feature vector.

To this end, a computing model, which can be trained before the execution of the method according to at least one embodiment of the invention by using a machine learning algorithm, can be held in a memory, in a local or central location. Training is, for example, performed by way of sample images and/or inputs by a user so that the algorithm is subsequently able independently to detect features in image recordings or detect function parameter.

Consequently, step S6 can comprise the creation of a texture metric for each tissue region GB. Herein, the texture analysis comprises the analysis of image element intensity values for the tissue region under consideration and the derivation of a spatial distribution thereof. The texture metric represents a measure for this spatial distribution, for example, the texture metric entails different moments of these image element intensities.

As mentioned in the introduction, it is possible for a plurality of image recordings to be combined to form a constructed medical image recording in order to obtain a desired image content or for a plurality of medical image recordings to be available. In many cases, step S5 can comprise a texture analysis based on the plurality of recordings or the plurality of image recordings in particular in cases in which different medical image recordings correspond to different recording embodiments, for example temporal phases, i.e. different time phases of an image recording, or different detected energy bands. The different image recordings can be acquired with or without contrast medium administration. A feature vector can comprise a plurality of texture metrics for a plurality of different parts or regions of the tissue to be examined, in particular a plurality of tissue regions.

For the purposes of at least one embodiment of the invention, a texture metric can comprise: an average, maximum, minimum image element intensity, a measure of uniformity, entropy in the sense of an irregularity in a gray-scale histogram, a standard-deviation of a gray-scale histogram, a skew in the sense of asymmetry of a gray-scale histogram, a curvature or flatness of a gray-scale histogram, an energy measure or a planar moment of inertia (for example pixel refresh rate and/or a measure of order), correlation (for example a measure for linear dependence of gray scale values), run-length matrix (for example a pixel texture in a specific spatial direction), contrast, roughness (for example as a measure for edge density), heterogeneity (for example as a measure for the presence of edges) or the like. The texture metric is preferably ascertained for each of the tissue regions GB in the medical image recording.

For the purposes of embodiments of the invention, 'image element' should include both pixels and voxels.

If there are a plurality of medical image recordings, according to at least one embodiment of the invention, the described method can optionally branch into a repeat loop R, wherein the method is repeated with the steps S1 to S5 until all the medical image recordings available for the derivation of the local tissue function of the tissue to be examined have been evaluated. In a further optional step S6, function parameters ascertained according to the invention can be compared, wherein the values were ascertained for the function parameters for medical image recordings which were acquired with a time offset. For example, it is possible to compare the same function parameter for medical image recordings in a first examination with medical recordings in a follow-up examination at a later time. The comparison enables the identification of local, i.e. also minute changes to the tissue over the observation period. The comparison can preferably be performed using machine learning methods.

As a result of the objectivization of the state information relating to the tissue to be examined and the spatial resolution that can be set as desired, the described method is in particular suitable for observing tissue states, for example fat content or bone density and in particular for monitoring the course of novel tumor therapy while dispensing with previous evaluation criteria, such as RECIST.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

Even if not explicitly stated, where advisable and in accordance with the invention, individual example embodiments, individual partial embodiments or features thereof can be combined with one another or replaced by one another without leaving the scope of the present invention. Where transferrable, advantages of the invention described with respect to an example embodiment are also applicable, without this being explicitly stated, to other example embodiments. Furthermore, the use of the indefinite article "a" or "an" does not preclude the possibility that the features in question may also be present on a multiple basis. Similarly, the possibility is not precluded that elements of the present invention present as individual units comprise a plurality of interface subcomponents, which could also be spatially distributed.

What is claimed is:

1. A method for determining a local tissue function of tissue in a body region of interest of an examination object, the method comprising:
   segmenting an outer contour of the tissue using at least one medical image recording representing the body region of interest of the examination object including the tissue, to produce a segmented tissue;
   subdividing the segmented tissue into at least two subdivided tissue regions; and
   ascertaining a function parameter relating to a tissue function from a first point in time to a second point in time for each of the at least two tissue regions, wherein the at least two subdivided tissue regions are arranged in slices such that a first subdivided tissue region of the at least two tissue regions completely encloses a second subdivided tissue region of the at least two tissue regions.

2. The method of claim 1, wherein the outer contour of each of the at least two subdivided tissue regions each has a same shape as the outer contour of the segmented tissue.

3. The method of claim 2, wherein the outer contour of at least one of the at least two tissue regions has a distance from at least one other of the at least two tissue regions within a range of 0.2 mm to 2.0 mm.

4. The method of claim 2, wherein the subdividing of the segmented tissue is performed using a morphological operation.

5. The method of claim 1, wherein the outer contour of at least one of the at least two subdivided tissue regions has a distance from at least one other of the at least two tissue regions within a range of 0.2 mm to 2.0 mm.

6. The method of claim 1, wherein the subdividing of the segmented tissue is performed using a morphological operation.

7. The method of claim 1, wherein the segmented tissue comprises a medical lesion.

8. The method of claim 1, wherein the function parameter is at least one parameter from a group of parameters including: blood flow, iodine-accumulation, iron accumulation, calcium density, and fat content.

9. The method of claim 1, wherein the function parameter is at least one parameter for texture analysis selected from a group of parameters including: average density, moments, heterogeneity, entropy, and fractal dimension.

10. The method of claim 9, wherein the ascertaining of the function parameter comprises ascertaining of a texture analysis, and wherein the ascertaining of the texture analysis comprises:
    determining a feature vector based on intensity values of image elements of the medical image recording,
    applying a machine learning method to the feature vector, and
    generating the function parameter as a result of the machine learning method.

11. The method of claim 1, wherein the medical image recording is an image recording selected from a group of image recordings including: single-energy recording, multispectral computed-tomography recording, perfusion-computed-tomography recording, ultrasound recording, magnetic-resonance recording and perfusion-magnetic-resonance recording.

12. A memory, storing a computer program with program code for carrying out the method of claim 1 when the computer program is executed on a computer.

13. A non-transitory computer-readable data carrier storing program code of a computer program for carrying out the method of claim 1 when the computer program is executed on a computer.

14. The method of claim 1, wherein the ascertaining of the function parameter comprises ascertaining of a texture analysis, and wherein the ascertaining of the texture analysis comprises:
    determining a feature vector based on intensity values of image elements of the medical image recording,
    applying a machine learning method to the feature vector, and
    generating the function parameter as a result of the machine learning method.

15. The method of claim 1, wherein the function parameter is at least a parameter of blood flow, iodine-accumulation, iron-accumulation, calcium density, fat content.

16. A computing unit for determining a tissue function of tissue in a region of interest of an examination object, the computing unit comprising:

a memory storing program computer-readable instructions; and one or more processors configured to execute the instructions such that the one or more processors are configured to, segment an outer contour of the tissue using at least one medical image recording representing the body region of interest of the examination object including the tissue, to produce a segmented tissue, subdivide the segmented tissue into at least two subdivided tissue regions, and ascertain a function parameter relating to a tissue function from a first point in time to a second point in time for each of the at least two subdivided tissue regions.

17. A medical imaging system comprising the computing unit of claim 16.

18. The computing unit of claim 16, wherein the ascertaining of the function parameter comprises ascertaining of a texture analysis and wherein the one or more processors is further configured to execute the instructions such that the one or more processors are further configured to ascertain of the texture analysis by at least:

determining a feature vector based on intensity values of image elements of the medical image recording, applying a machine learning method to the feature vector, and generating the function parameter as a result of the machine learning method.

19. The computing unit of claim 16, wherein the at least two tissue regions are arranged in slices such that a first tissue region of the at least two tissue regions completely encloses a second tissue region of the at least two tissue regions.

20. The computing unit of claim 16, wherein the outer contour of each of the at least two tissue regions each has a same shape as the outer contour of the segmented tissue.

21. The computing unit of claim 16, wherein the ascertaining of the function parameter comprises ascertaining at least a parameter of blood flow, iodine-accumulation, iron-accumulation, calcium density, fat content.

* * * * *